United States Patent
Fukuda et al.

(10) Patent No.: US 11,521,737 B2
(45) Date of Patent: Dec. 6, 2022

(54) HOSPITAL VISIT SUPPORT DEVICE, METHOD, PROGRAM, AND SYSTEM

(71) Applicant: FUJIFILM CORPORATION, Tokyo (JP)

(72) Inventors: Takeshi Fukuda, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/093,646

(22) Filed: Nov. 10, 2020

(65) Prior Publication Data

US 2021/0151173 A1  May 20, 2021

(30) Foreign Application Priority Data

Nov. 19, 2019 (JP) .............................. JP2019-208497

(51) Int. Cl.
 *G16H 40/20* (2018.01)
 *G16H 50/30* (2018.01)
 *G16H 20/10* (2018.01)
 *G16H 10/60* (2018.01)

(52) U.S. Cl.
 CPC ............. *G16H 40/20* (2018.01); *G16H 50/30* (2018.01)

(58) Field of Classification Search
 CPC ...................................................... G16H 40/20
 See application file for complete search history.

(56) References Cited

U.S. PATENT DOCUMENTS

| | | | |
|---|---|---|---|
| 2008/0103371 A1* | 5/2008 | Rosenblum | G16H 20/30 600/300 |
| 2014/0052463 A1* | 2/2014 | Cashman | G06Q 10/1095 705/2 |
| 2020/0411145 A1* | 12/2020 | Oda | H04L 63/083 |
| 2021/0125152 A1* | 4/2021 | Sproat | G16H 40/20 |
| 2021/0134462 A1* | 5/2021 | Fukuda | G16H 50/30 |

FOREIGN PATENT DOCUMENTS

JP  2003-178142 A  6/2003

\* cited by examiner

*Primary Examiner* — Joseph H Feild
*Assistant Examiner* — Pameshanand Mahase
(74) *Attorney, Agent, or Firm* — Solaris Intellectual Property Group, PLLC

(57) ABSTRACT

A pet health management device includes an RW controller as an acquisition unit and a screen distribution controller as a distribution controller. The RW controller reads pet information from a storage device to acquire a scheduled hospital visit date to an animal hospital of a pet. The screen distribution controller distributes a pet health management screen with a message prompting a hospital visit of the pet and including assumed symptom information indicating a symptom assumed in a case where there is no hospital visit of the pet on the scheduled hospital visit date, to an owner terminal according to the scheduled hospital visit date.

9 Claims, 20 Drawing Sheets

FIG. 5

MESSAGE TABLE 43

| DISTRIBUTION DATE | FIXED FORM MESSAGE |
|---|---|
| FIVE DAYS BEFORE SCHEDULED HOSPITAL VISIT DATE | HOW IS YOUR [PET NAME]? THERE ARE FIVE DAYS LEFT UNTIL [SCHEDULED HOSPITAL VISIT DATE] WHICH IS NEXT RESERVATION DATE FOR MEDICAL CARE. PLEASE DO NOT HESITATE TO CONTACT US IN CASE WHERE THERE ARE ANY CONCERNS ABOUT SYMPTOM. |
| ONE DAY BEFORE SCHEDULED HOSPITAL VISIT DATE | HOW IS YOUR [PET NAME]? TOMORROW IS [SCHEDULED HOSPITAL VISIT DATE] WHICH IS RESERVATION DATE FOR MEDICAL CARE. [CHRONIC DISEASE] IS [ASSUMED SYMPTOM INFORMATION]. PLEASE BE CAREFUL TOMORROW. |
| ONE DAY AFTER SCHEDULED HOSPITAL VISIT DATE | HOW IS YOUR [PET NAME]? THERE SEEMS NO HOSPITAL VISIT ON [SCHEDULED HOSPITAL VISIT DATE] WHICH IS YESTERDAY'S RESERVATION DATE FOR MEDICAL CARE. DRUG MAY RUN OUT. [CHRONIC DISEASE] IS [ASSUMED SYMPTOM INFORMATION]. PLEASE VISIT HOSPITAL AS SOON AS POSSIBLE. |
| FIVE DAYS AFTER SCHEDULED HOSPITAL VISIT DATE | HOW IS YOUR [PET NAME]? THERE SEEMS NO HOSPITAL VISIT ON [SCHEDULED HOSPITAL VISIT DATE] WHICH IS PREVIOUS RESERVATION DATE FOR MEDICAL CARE. DRUG MAY RUN OUT FOR LONG TIME. [CHRONIC DISEASE] IS [ASSUMED SYMPTOM INFORMATION]. PLEASE VISIT HOSPITAL IMMEDIATELY. |

ASSUMED SYMPTOM INFORMATION TABLE (44)

| CHRONIC DISEASE | ASSUMED SYMPTOM INFORMATION | ... |
|---|---|---|
| CHRONIC ENTEROPATHY | DIARRHEA, VOMITING, LOSS OF APPETITE, SWELLING OF WHOLE BODY, OR THE LIKE MAY OCCUR AND SERIOUS SYMPTOM MAY OCCUR IN CASE WHERE MEDICAL TREATMENT IS NEGLECTED. | |
| BRONCHIAL ASTHMA | REPEATED ATTACK MAY OCCUR IN CASE WHERE MEDICAL TREATMENT IS NEGLECTED AND COMPLICATIONS WITH OTHER RESPIRATORY DISEASE SUCH AS PNEUMONIA MAY CAUSE DEATH. | |
| DIABETES | FREQUENT URINATION, DIARRHEA, VOMITING, WEIGHT LOSS, OR THE LIKE MAY OCCUR AND COMPLICATIONS SUCH AS CATARACT, GANGRENE, NEUROPATHY, AND LIVER DYSFUNCTION DEVELOP IN CASE WHERE MEDICAL TREATMENT IS NEGLECTED. | ... |

57

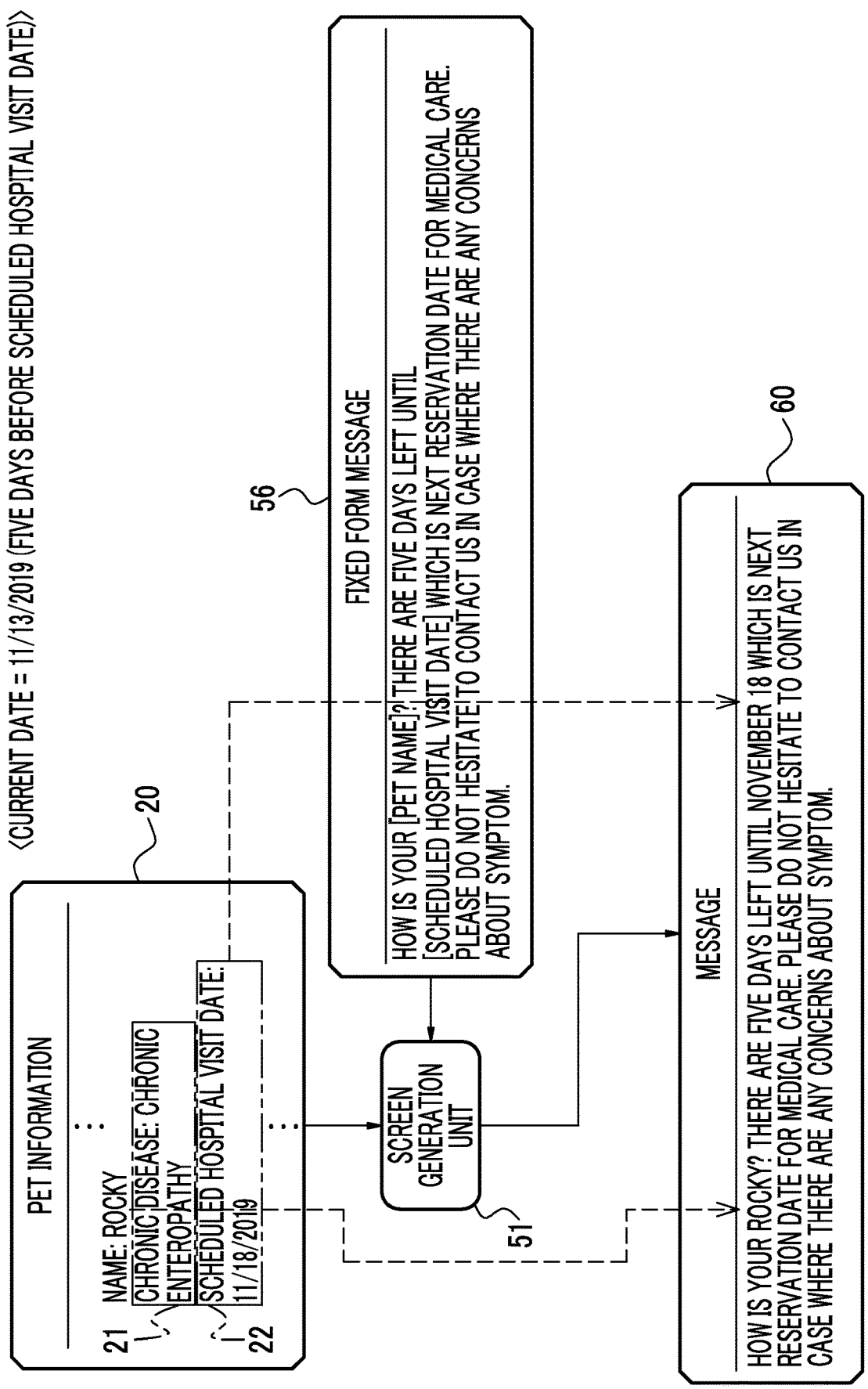

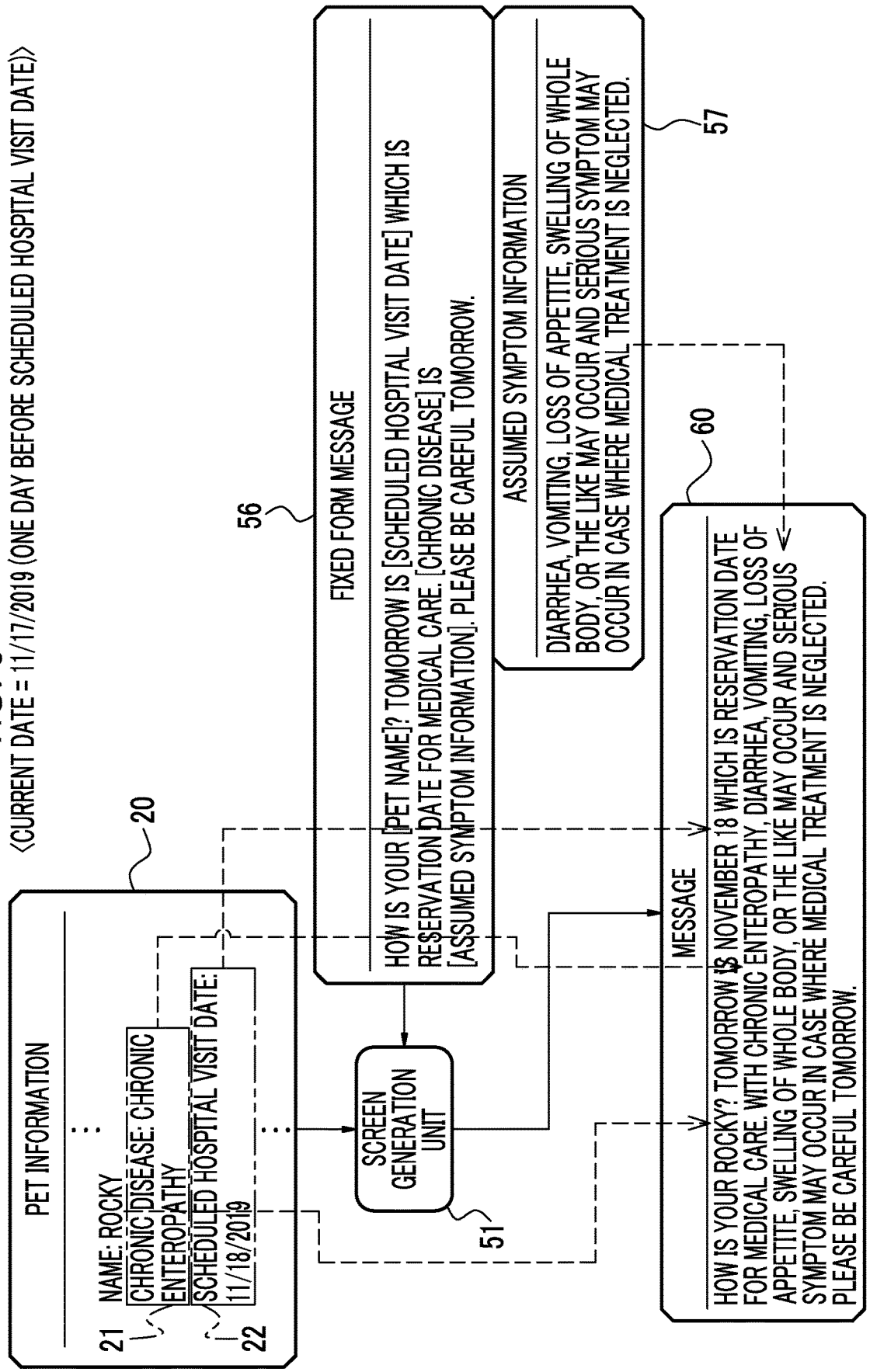

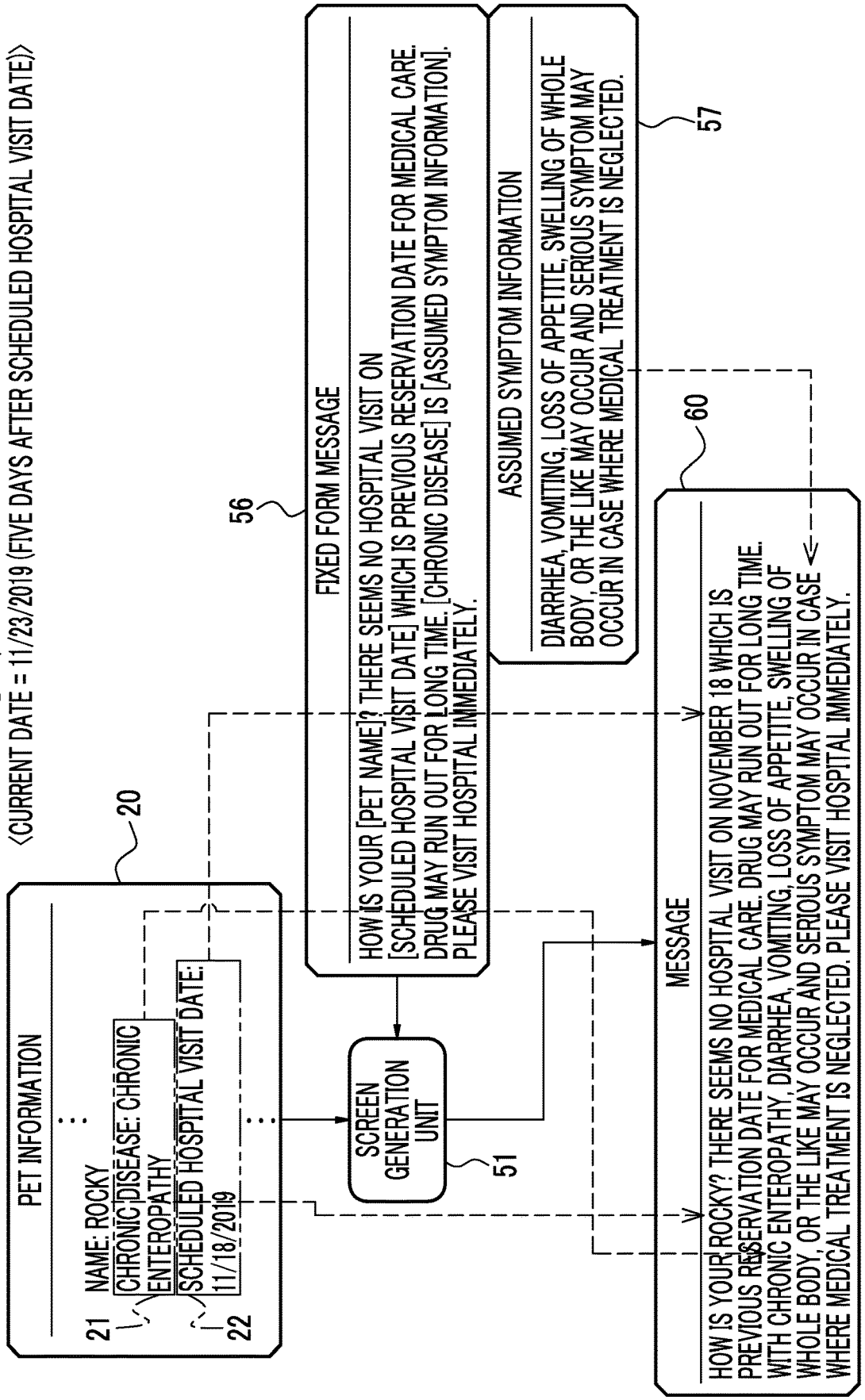

FIG. 11

| | PET HEALTH MANAGEMENT | | | | | |
|---|---|---|---|---|---|---|
| | PET INFORMATION | | | | | |
| | ROCKY SEVEN YEARS OLD MALE GOLDEN RETRIEVER | | | | | |
| | CALENDER | | | | | |
| 2019 | | | NOVEMBER | | | |
| SUNDAY | MONDAY | TUESDAY | WEDNESDAY | THURSDAY | FRIDAY | SATURDAY |
| 27 | 28 | 29 | 30 | 31 | 1 | 2 |
| 3 | 4 (83) | 5 | 6 | 7 | 8 | 9 |
| 10 | 11 (84) | 12 | 13 | 14 | 15 | 16 (84) |
| 17 | 18 (83) | 19 | 20 | 21 | 22 | 23 |
| 24 | 25 | 26 | 27 | 28 | 29 | 30 |

MESSAGE

HOW IS YOUR ROCKY?
THERE ARE FIVE DAYS LEFT UNTIL NOVEMBER 18 WHICH IS NEXT RESERVATION DATE FOR MEDICAL CARE.
PLEASE DO NOT HESITATE TO CONTACT US IN CASE WHERE THERE ARE ANY CONCERNS ABOUT SYMPTOM.

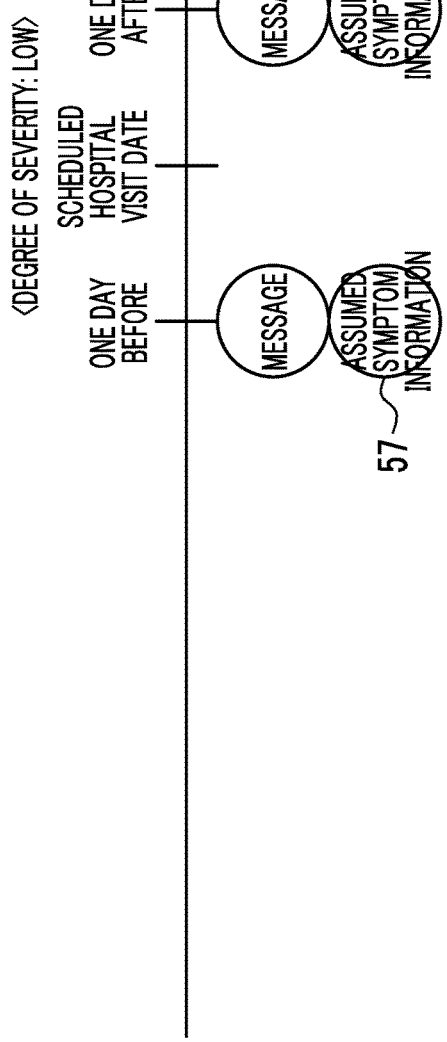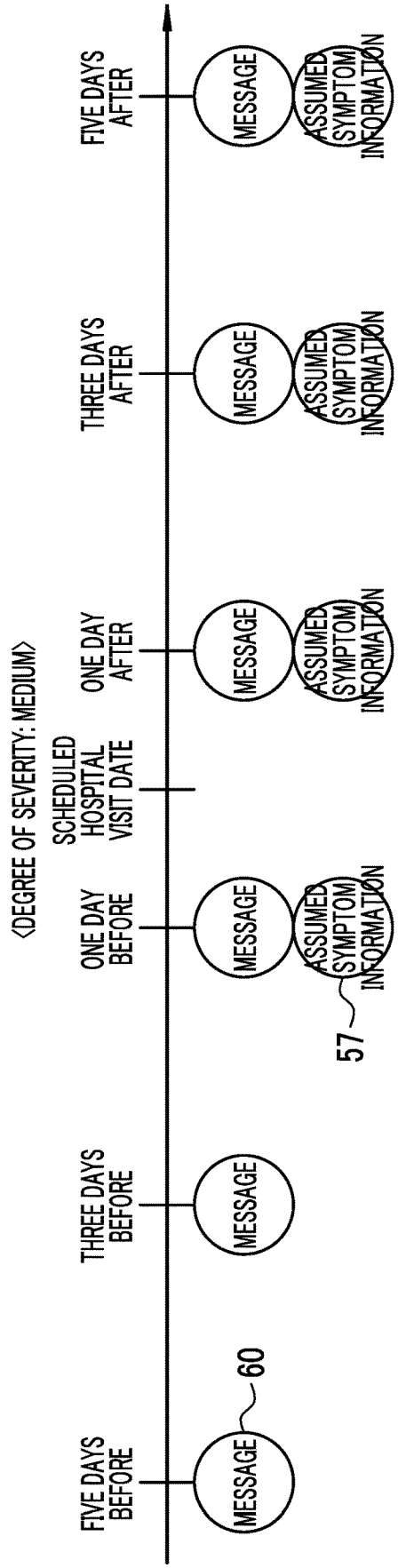

FIG. 19

ASSUMED SYMPTOM INFORMATION TABLE 100

| CHRONIC DISEASE | BREED | ASSUMED SYMPTOM INFORMATION | ... |
|---|---|---|---|
| CHRONIC ENTEROPATHY | SHIBA INU | DIARRHEA, VOMITING, LOSS OF APPETITE, SWELLING OF WHOLE BODY, OR THE LIKE MAY OCCUR AND SERIOUS SYMPTOM MAY OCCUR IN CASE WHERE MEDICAL TREATMENT IS NEGLECTED. SHIBA INU REQUIRES PARTICULARLY CAREFUL FOLLOW-UP OBSERVATION. | |
| | OTHER THAN SHIBA INU | DIARRHEA, VOMITING, LOSS OF APPETITE, SWELLING OF WHOLE BODY, OR THE LIKE MAY OCCUR AND SERIOUS SYMPTOM MAY OCCUR IN CASE WHERE MEDICAL TREATMENT IS NEGLECTED. | |
| DIABETES | BEAGLE POODLE DACHSHUND MINIATURE SCHNAUZER | FREQUENT URINATION, DIARRHEA, VOMITING, WEIGHT LOSS, OR THE LIKE MAY OCCUR AND COMPLICATIONS SUCH AS CATARACT, GANGRENE, NEUROPATHY, AND LIVER DYSFUNCTION DEVELOP IN CASE WHERE MEDICAL TREATMENT IS NEGLECTED. BEAGLE, POODLE, DACHSHUND, MINIATURE SCHNAUZER ARE PRONE TO CONGENITAL CAUSES AND NEED SPECIAL ATTENTION. | |
| | OTHER THAN ABOVE | FREQUENT URINATION, DIARRHEA, VOMITING, WEIGHT LOSS, OR THE LIKE MAY OCCUR AND COMPLICATIONS SUCH AS CATARACT, GANGRENE, NEUROPATHY, AND LIVER DYSFUNCTION DEVELOP IN CASE WHERE MEDICAL TREATMENT IS NEGLECTED. | |
| ... | | | |

HOSPITAL VISIT SUPPORT DEVICE, METHOD, PROGRAM, AND SYSTEM

CROSS-REFERENCE TO RELATED APPLICATIONS

The present application claims priority under 35 U.S.C. § 119 to Japanese Patent Application No. 2019-208497 filed on Nov. 19, 2019. The above application is hereby expressly incorporated by reference, in its entirety, into the present application.

BACKGROUND

1. Technical Field

A technique of the present disclosure relates to a hospital visit support device, method, program, and system.

2. Description of the Related Art

JP2003-178142A describes a technique of distributing a message prompting a hospital visit from a hospital terminal to a terminal of a patient suffering from a chronic disease.

SUMMARY

The present inventors are investigating a technique of effectively promoting a hospital visit of a pet to an animal hospital. In this case, a simple message such as "Next scheduled hospital visit date is what month and day" is not sufficient. The pet cannot tell a symptom verbally, of course. For this reason, an owner of the pet may underestimate the symptom of the pet and lose the will to bring the pet to the hospital according to the message. Therefore, in a case where a target is the pet, it is necessary to more strongly motivate the owner to bring the pet to the animal hospital.

An object of the technique of the present disclosure is to provide a hospital visit support device, method, program, and system capable of more strongly motivating an owner of a pet to bring the pet to an animal hospital.

In order to achieve the above-mentioned object, a hospital visit support device according to the present disclosure comprises an acquisition unit that acquires a scheduled hospital visit date to an animal hospital of a pet suffering from a chronic disease, and a distribution controller that controls a distribution of message information related to a message prompting a hospital visit of the pet and including assumed symptom information indicating a symptom assumed in a case where there is no hospital visit of the pet on the scheduled hospital visit date, to an owner terminal owned by an owner of the pet according to the scheduled hospital visit date.

It is preferable that the distribution controller distributes the message information also after the scheduled hospital visit date in the case where there is no hospital visit of the pet on the scheduled hospital visit date, in addition to before the scheduled hospital visit date.

It is preferable that the distribution controller differentiates a distribution frequency of the message information distributed before the scheduled hospital visit date and a distribution frequency of the message information distributed after the scheduled hospital visit date.

It is preferable that the distribution controller increases a distribution frequency of the message information as a degree of severity of the chronic disease is higher.

It is preferable that there are cases where the message includes and does not include the assumed symptom information depending on a difference between the scheduled hospital visit date and a distribution date of the message information.

It is preferable that the assumed symptom information for the same chronic disease differs depending on a breed of the pet.

The hospital visit support method according to the present disclosure comprises an acquisition step of acquiring a scheduled hospital visit date to an animal hospital of a pet suffering from a chronic disease, and a distribution step of distributing message information related to a message prompting a hospital visit of the pet and including assumed symptom information indicating a symptom assumed in a case where there is no hospital visit of the pet on the scheduled hospital visit date, to an owner of the pet according to the scheduled hospital visit date.

It is preferable that the hospital visit support method further comprises a display step of performing a display based on the distributed message information.

A hospital visit support program according to the present disclosure causing a computer to function as an acquisition unit that acquires a scheduled hospital visit date to an animal hospital of a pet suffering from a chronic disease, and a distribution controller that controls a distribution of message information related to a message prompting a hospital visit of the pet and including assumed symptom information indicating a symptom assumed in a case where there is no hospital visit of the pet on the scheduled hospital visit date, to an owner terminal owned by an owner of the pet according to the scheduled hospital visit date.

A hospital visit support system according to the present disclosure comprises a hospital visit support device that acquires a scheduled hospital visit date to an animal hospital of a pet suffering from a chronic disease, and distributes message information related to a message prompting a hospital visit of the pet and including assumed symptom information indicating a symptom assumed in a case where there is no hospital visit of the pet on the scheduled hospital visit date, according to the scheduled hospital visit date, and an owner terminal that is owned by an owner of the pet and performs a display based on the distributed message information.

According to the technique of the present disclosure, it is possible to provide a hospital visit support device, method, program, and system capable of more strongly motivating the owner of the pet to bring the pet to the animal hospital.

BRIEF DESCRIPTION OF THE DRAWINGS

Exemplary embodiments according to the technique of the present disclosure will be described in detail based on the following figures, wherein:

FIG. 5 is a diagram showing a message table;

FIG. 6 is a diagram showing an assumed symptom information table;

FIG. 7 is a diagram showing details of message creation processing by a screen generation unit in a case where a current date is five days before a scheduled hospital visit date;

FIG. 8 is a diagram showing details of message creation processing by the screen generation unit in a case where the current date is one day before the scheduled hospital visit date;

FIG. 9 is a diagram showing details of message creation processing by the screen generation unit in a case where the current date is five days after the scheduled hospital visit date;

FIG. 11 is a diagram showing a pet health management screen in the case of the example of FIG. 7;

FIG. 16A shows an example in which the distribution frequency of the message information to be distributed after the scheduled hospital visit date is higher than the distribution frequency of the message information to be distributed before the scheduled hospital visit date, and FIG. 16B shows an example in which the distribution frequency of the message information to be distributed after the scheduled hospital visit date is lower than the distribution frequency of the message information to be distributed before the scheduled hospital visit date, respectively;

FIGS. 18A and 18B are diagrams showing a distribution frequency of message information according to a degree of severity of a chronic disease. FIG. 18A shows a case where the degree of severity is "low", FIG. 18B shows a case where the severity is "medium"

FIG. 19 is a diagram showing an assumed symptom information table according to a fourth embodiment; and FIG. 20 is a diagram showing a pet health management screen provided with a link to a medical care reservation site.

DETAILED DESCRIPTION

First Embodiment

Figure 1:
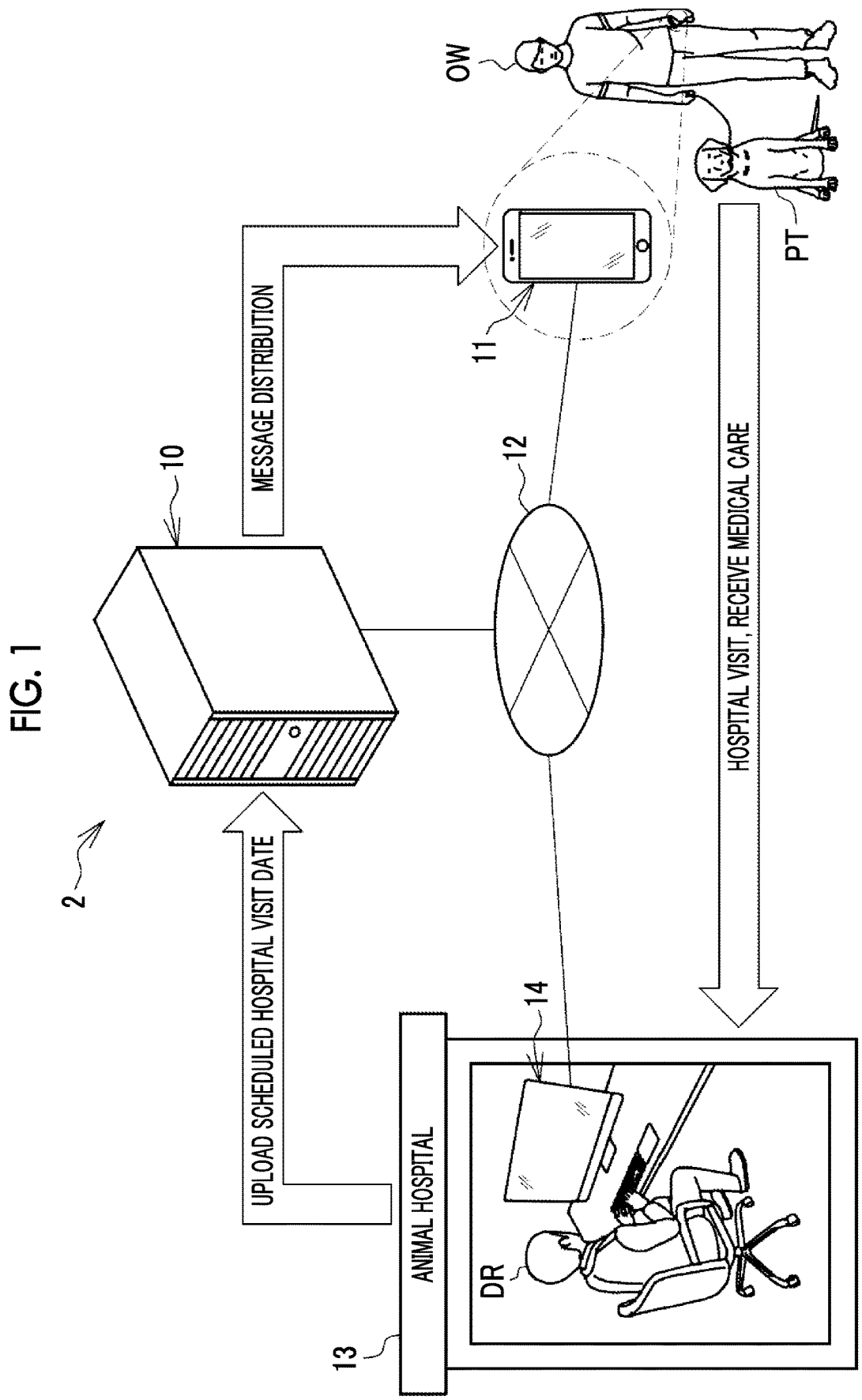
FIG. 1 is a diagram showing a pet health management system.

In FIG. 1, a pet health management system 2 is a system that manages a health condition of a pet PT suffering from a chronic disease. The pet health management system 2 includes a pet health management device 10 and an owner terminal 11 owned by an owner OW of the pet PT. The pet health management system 2 is an example of a "system" according to a technique of the present disclosure. The chronic disease refers to a disease that gradually develops and in which a medical treatment period is indefinite and a cure is rare.

The pet health management device 10 is, for example, a server computer and is an example of a "hospital visit support device" according to the technique of the present disclosure. The owner terminal 11 is, for example, a smartphone. The pet health management device 10 and the owner terminal 11 are communicably connected through a network 12. The network 12 is, for example, a wide area network (WAN) such as the Internet or a public communication network.

A hospital terminal 14 operated by a doctor DR or the like in an animal hospital 13 is also connected to the network 12. The hospital terminal 14 is, for example, a desktop personal computer. There are actually a plurality of pets PT, owners OW, and animal hospitals 13. Therefore, there are actually a plurality of owner terminals 11 and hospital terminals 14. In this case, an installation place and an operation main body of the pet health management device 10 may be a data center operated by a company other than the animal hospital 13 or may be one of a plurality of animal hospitals 13.

The owner OW visits the animal hospital 13 with the pet PT and causes the pet PT to receive medical care from the doctor DR at the animal hospital 13. The doctor DR operates the hospital terminal 14 to input a medical care result of the pet PT. The doctor DR inputs pet information 20 (refer to FIG. 2) which is information on the pet PT, owner information 25 (refer to FIG. 2) which is information on the owner OW, and the like, in addition to the medical care result. The hospital terminal 14 uploads the input medical care result, pet information 20, owner information 25, and the like to the pet health management device 10.

The pet information 20 includes a next scheduled hospital visit date 22 (refer to FIG. 2) of the pet PT. The owner information 25 includes owner terminal identification information 26 (refer to FIG. 2). The pet health management device 10 generates a message 60 (refer to FIG. 7 to FIG. 9 and the like) prompting the hospital visit of the pet PT according to the scheduled hospital visit date 22. A pet health management screen 55 (refer to FIGS. 4 and 11 to 13) that displays the generated message 60 is distributed to the owner terminal 11 by relying on the owner terminal identification information 26. The pet health management screen 55 that displays the message 60 is an example of "message information" according to the technique of the present disclosure.

Figure 2:
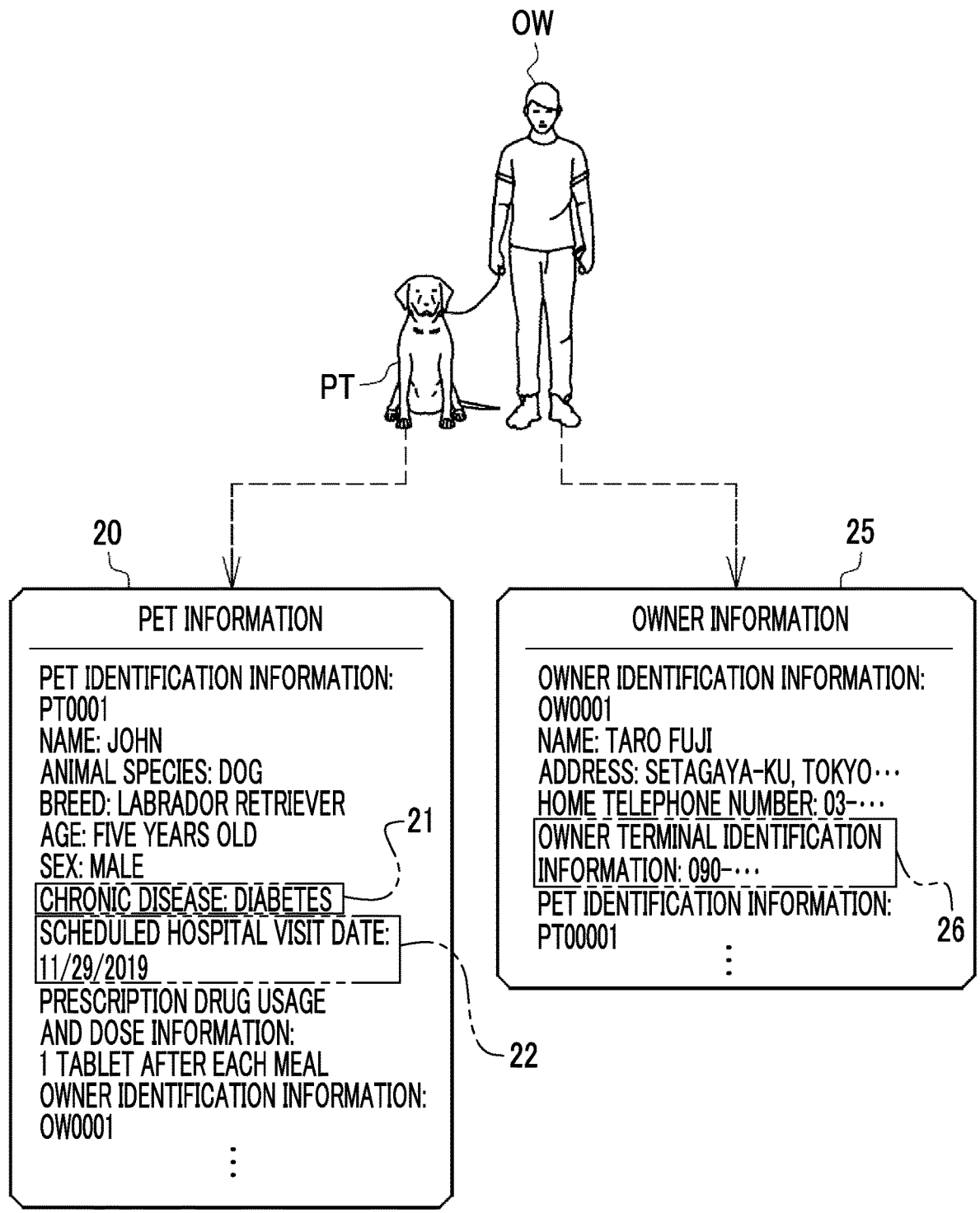
FIG. 2 is a diagram showing pet information and owner information.

In FIG. 2, pet identification information, name of pet PT, animal species, breed, age, sex, suffered chronic disease 21, scheduled hospital visit date 22, prescription drug usage and dose information, owner identification Information, and the like are registered in the pet information 20. The pet identification information is a combination of a symbol and a number for identifying each pet PT. The animal species includes a dog and a cat. In a case where the animal species is the dog, examples of the breed include Labrador Retriever, Yorkshire Terrier, Papillon, Maltese, Chihuahua, and Shiba Inu. In a case where the animal species is the cat, examples of the breed include Ragdoll, Himalayan, and Ragamuffin. The scheduled hospital visit date 22 is a reservation date for next medical care for the pet PT, which is determined between the doctor DR and the owner OW after the medical care for the pet PT. The owner identification information is a combination of a symbol and a number for identifying each owner OW. Most of the pet information 20, such as name, animal species, breed, age, sex, chronic disease 21, and owner identification information, is registered at the time of first medical care for the pet PT or the like. On the contrary, the scheduled hospital visit date 22 is updated every time a next hospital visit is determined after each time of the medical care. The prescription drug usage and dose information is also updated every time the drug is prescribed. A vaccination history, a hospitalization history, a surgery history (including castration history), and the like are also registered in the pet information 20, in addition to the above.

The owner identification information, name, address, and home telephone number of the owner OW, owner terminal identification information 26, pet identification information, and the like are registered in the owner information 25. The owner terminal identification information 26 is a telephone number of the smartphone which is the owner terminal 11 in this example. The owner information 25 is registered at the time of the first medical care for the pet PT or the like. In a case where the owner OW has a plurality of pets PT, that is, a so-called multi-headed pet and the plurality of pets PT receive the medical care at the animal hospital 13, pet identification information for the plurality of pets is registered in the owner information 25.

The owner identification information is registered in the pet information 20, in addition to the pet identification information. The pet identification information is registered in the owner information 25, in addition to the owner identification information. Therefore, the pet information 20 and the owner information 25 are associated with each other by the pet identification information and the owner identification information.

Figure 3:
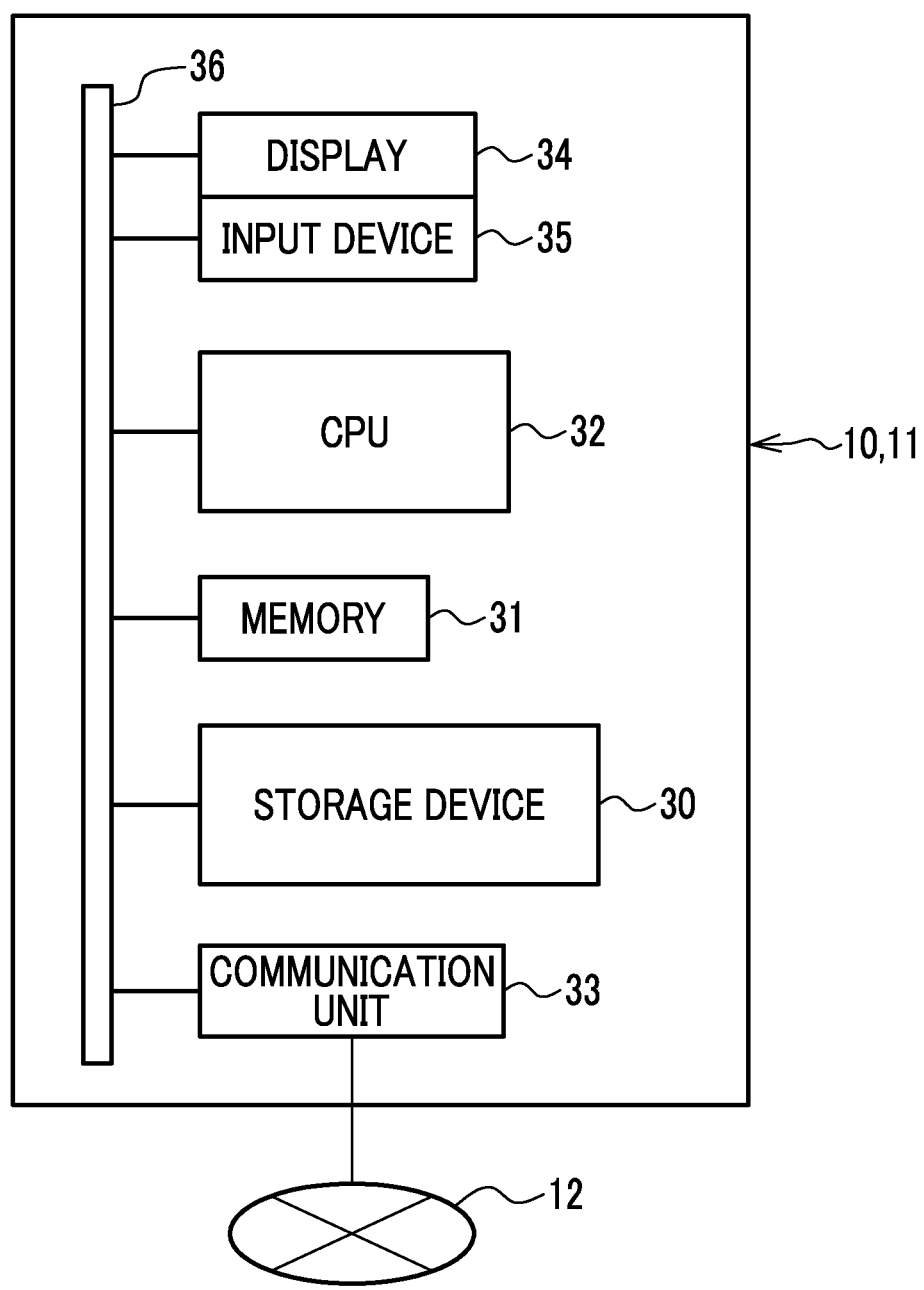
FIG. 3 is a block diagram showing computers configuring a pet health management device and an owner terminal.

In FIG. 3, computers configuring the pet health management device 10 and the owner terminal 11 have basically the same configuration and comprise a storage device 30, a memory 31, a central processing unit (CPU) 32, a communication unit 33, a display 34, and an input device 35. These are interconnected through a busline 36.

The storage device 30 is a hard disk drive built in or connected to, through a cable or a network, the computers configuring the pet health management device 10 and the owner terminal 11. Alternatively, the storage device 30 is a disk array in which a plurality of hard disk drives are connected in series. The storage device 30 stores a control program such as an operating system, various application programs (hereinafter abbreviated as application program (AP)), various pieces of data attached to these programs, and the like. A solid state drive may be used instead of the hard disk drive.

The memory 31 is a work memory for a CPU 32 to execute processing. The CPU 32 loads the program stored in the storage device 30 into the memory 31 and executes the processing according to the program to integrally control the respective components of the computer.

The communication unit 33 is a network interface that controls transmission of various types of information through the network 12. The display 34 displays various screens. The various screens are provided with an operation function by a graphical user interface (GUI). The computers configuring the pet health management device 10 and the owner terminal 11 receive an input of an operation instruction from the input device 35 through the various screens. The input device 35 is a keyboard, a mouse, a touch panel, or the like.

In the following description, each component of the computer configuring the pet health management device 10 is distinguished by assigning a suffix "A" to a reference numeral thereof and each component of the computer configuring the owner terminal 11 is distinguished by assigning a suffix "B" to a reference numeral thereof, respectively.

Figure 4:
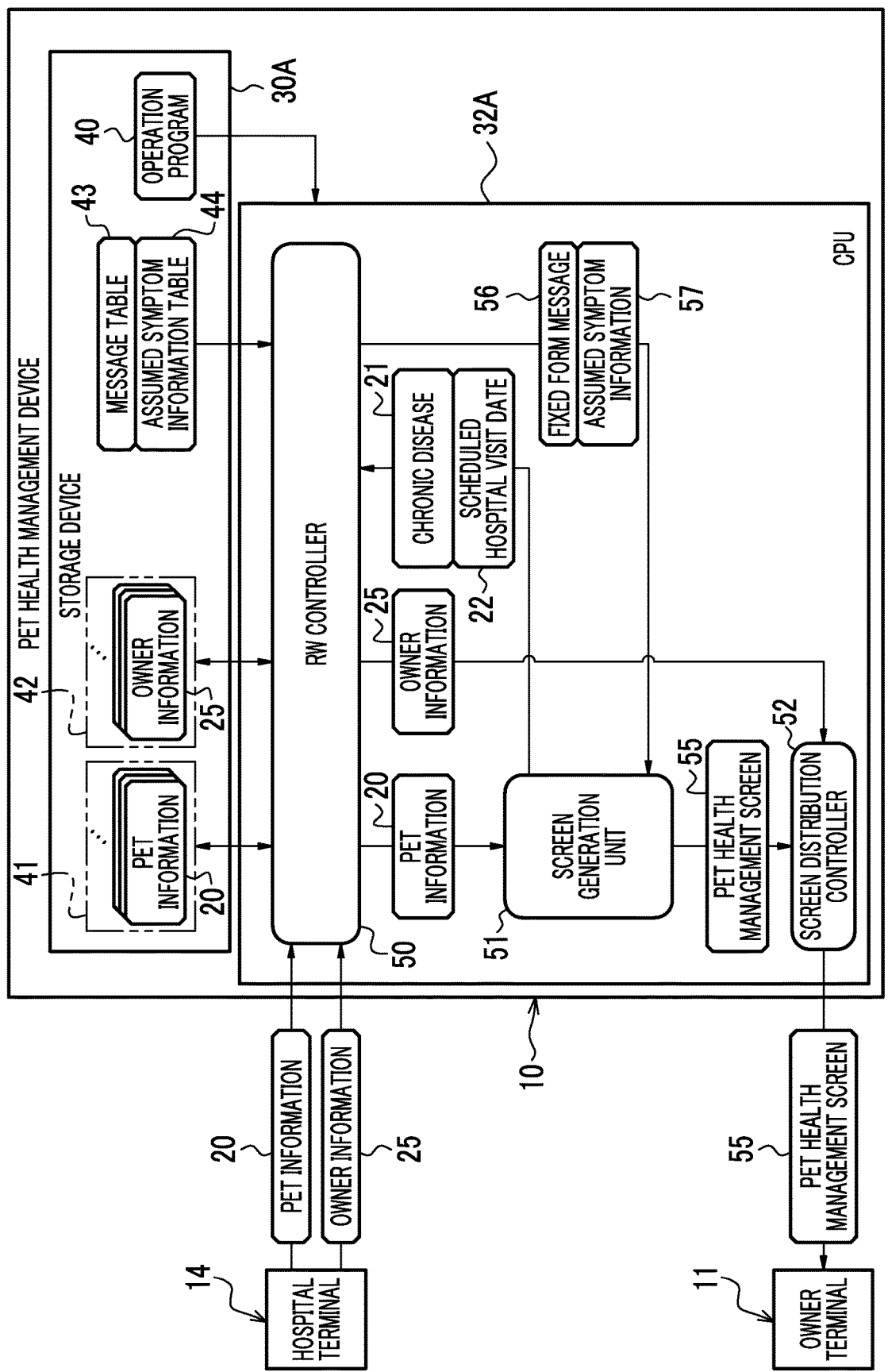
FIG. 4 is a block diagram showing a processing unit of a CPU of the pet health management device.

In FIG. 4, an operation program 40 is stored in a storage device 30A of the pet health management device 10. The operation program 40 is an AP for causing the computer to function as the pet health management device 10. That is, the operation program 40 is an example of the "program" according to the technique of the present disclosure. The storage device 30A also stores a pet information group 41, an owner information group 42, a message table 43, and an assumed symptom information table 44, in addition to the operation program 40.

In a case where the operation program 40 is activated, a CPU 32A of the pet health management device 10 cooperates with the memory 31 and the like to function as a read and write (hereinafter abbreviated as RW) controller 50, a screen generation unit 51, and a screen distribution controller 52.

The RW controller 50 controls storage of various types of information in the storage device 30A and reading of the various types of information in the storage device 30A. The RW controller 50 stores the pet information 20 and the owner information 25 uploaded from the hospital terminal 14 in the storage device 30A. Accordingly, the storage device 30A stores the pet information 20 of the plurality of pets PT as the pet information group 41 and the owner information 25 of the plurality of owners OW as the owner information group 42, respectively.

The RW controller 50 reads, from the storage device 30A, the pet information 20 of the pet PT to which the message 60 is required to be distributed, among the pet information 20 configuring the pet information group 41. The pet information 20 of the pet PT to which the message 60 is required to be distributed is the pet information 20 whose current date corresponds to any one of five days before, one day before, one day after, or five days after the registered scheduled hospital visit date 22. A case where the current date is one day or five days after the scheduled hospital visit date 22 is a case where there is no hospital visit of the pet PT on the scheduled hospital visit date 22 and the scheduled hospital visit date 22 is not updated. The RW controller 50 outputs the read pet information 20 to the screen generation unit 51.

The RW controller 50 reads the pet information 20 from the storage device 30A to acquire the scheduled hospital visit date 22. That is, the RW controller 50 is an example of the "acquisition unit" according to the technique of the present disclosure.

The RW controller 50 reads, from the storage device 30A, the owner information 25 associated with the pet information 20 of the pet PT to which the message 60 is required to be distributed, among the owner information 25 configuring the owner information group 42. The RW controller 50 outputs the read owner information 25 to the screen distribution controller 52.

The screen generation unit 51 generates various screens. The screen generation unit 51 outputs the generated various screens to the screen distribution controller 52.

The screen generation unit 51 outputs the scheduled hospital visit date 22 registered in the pet information 20 from the RW controller 50 to the RW controller 50 as a search key. The RW controller 50 reads, from the message table 43, a fixed form message 56 corresponding to the scheduled hospital visit date 22 from the screen generation unit 51. In a case where the current date corresponds to one day before, one day after, or five days after the scheduled hospital visit date 22, the screen generation unit 51 outputs, to the RW controller 50, the chronic disease 21 registered in the pet information 20 from the RW controller 50 as the search key. The RW controller 50 reads, from the assumed symptom information table 44, the assumed symptom information 57 corresponding to the chronic disease 21 from the screen generation unit 51. The assumed symptom information 57 indicates a symptom assumed in a case where there is no hospital visit of the pet PT on the scheduled hospital visit date 22. The RW controller 50 outputs the read fixed form message 56 and assumed symptom information 57 to the screen generation unit 51. The screen generation unit 51 creates the message 60 based on the pet information 20, the fixed form message 56, and the assumed symptom information 57. The pet health management screen 55 that displays the created message 60 is generated.

The screen distribution controller 52 controls a distribution of the various screens such as the pet health management screen 55 to the owner terminal 11. More specifically, the screen distribution controller 52 outputs the various screens in a form of screen data for web distribution created in a markup language such as Extensible Markup Language (XML). Accordingly, it is possible to browse the various screens on a web browser on the owner terminal 11. The screen distribution controller 52 specifies the owner terminal 11 of a distribution destination such as the pet health management screen 55 based on the owner terminal identification information 26 registered in the owner information 25. The screen distribution controller 52 is an example of the "distribution controller" according to the technique of the present disclosure. Another data description language such as JavaScript (registered trademark) Object Notation (JSON) may be employed instead of XML.

As shown in FIG. 5, the fixed form messages 56 corresponding to the four distribution dates of the message 60 of five days before, one day before, one day after, and five days after the scheduled hospital visit date 22 are registered in the message table 43. For example, the fixed form message 56 having a content of "How is your [pet name]? There are five days left until [scheduled hospital visit date] which is next reservation date for medical care. Please do not hesitate to contact us in a case where there are any concerns about symptom." is registered on the distribution date of five days before the scheduled hospital visit date 22. The fixed form message 56 having a content of "How is your [pet name]? Tomorrow is [scheduled hospital visit date] which is reservation date for medical care. [Chronic disease] is [assumed symptom information]. Please be careful tomorrow." is registered on the distribution date of one day before the scheduled hospital visit date 22. The assumed symptom information 57 is also included in the fixed form messages 56 of the distribution dates of one day after and five days after the scheduled hospital visit date 22. As described above, the assumed symptom information 57 may or may not be included depending on a difference between the scheduled hospital visit date 22 and the distribution date.

As shown in FIG. 6, the assumed symptom information 57 is registered for each chronic disease 21 in the assumed symptom information table 44. For example, in a case where the chronic disease 21 is chronic enteropathy, the assumed symptom information 57 having a content of "diarrhea, vomiting, loss of appetite, swelling of whole body, or the like may occur and a serious symptom may occur in a case where medical treatment is neglected." is registered. In a case where the chronic disease 21 is diabetes, the assumed symptom information 57 having a content of "frequent urination, diarrhea, vomiting, weight loss, or the like may occur and complications such as cataract, gangrene, neuropathy, and liver dysfunction develop in a case where medical treatment is neglected." is registered.

In the fixed form message 56, the name of the pet registered in the pet information 20, the scheduled hospital visit date 22, and the chronic disease 21 are respectively addressed to [pet name], [scheduled hospital visit date], and [chronic disease]. The assumed symptom information 57 read from the assumed symptom information table 44 by the RW controller 50 is addressed to the [assumed symptom information]. As described above, the fixed form message 56 is a template which is a source of the message 60.

FIGS. 7 to 9 show details of creation processing of the message 60 by the screen generation unit 51. FIGS. 7 to 9 illustrate a case where the pet name is "Rocky", the chronic disease 21 is "chronic enteropathy", and the scheduled hospital visit date 22 is "Nov. 18, 2019 (Nov. 18, 2019)".

FIG. 7 shows a case where the current date is Nov. 13, 2019, which is five days before the scheduled hospital visit date 22. In this case, according to the message table 43, the fixed form message 56 has the content of "How is your [pet name]? There are five days left until [scheduled hospital visit date] which is next reservation date for medical care. Please do not hesitate to contact us in a case where there are any concerns about the symptom." Therefore, the screen generation unit 51 addresses "Rocky" to [pet name] and "November 18" to [scheduled hospital visit date] of the fixed form message 56, respectively, to create the message 60 having a content of "How is your Rocky? There are five days left until November 18 which is next reservation date for medical care. Please do not hesitate to contact us in a case where there are any concerns about the symptom."

FIG. 8 shows a case where the current date is Nov. 17, 2019, which is one day before the scheduled hospital visit date 22. In this case, according to the message table 43, the fixed form message 56 has the content of "How is your [pet name]? Tomorrow is [scheduled hospital visit date] which is reservation date for medical care. [Chronic disease] is [assumed symptom information]. Please be careful tomorrow." Therefore, as in the case of FIG. 7, the screen generation unit 51 addresses "Rocky" to [pet name] and "November 18" to [scheduled hospital visit date] of the fixed form message 56, respectively. The screen generation unit 51 also addresses "chronic enteropathy" to the "chronic disease" of the fixed form message 56.

According to the assumed symptom information table 44, the assumed symptom information 57 for chronic enteropathy has the content of "diarrhea, vomiting, loss of appetite, swelling of whole body, or the like may occur and a serious symptom may occur in a case where medical treatment is neglected." For this reason, the screen generation unit 51 addresses "diarrhea, vomiting, loss of appetite, swelling of whole body, or the like may occur and a serious symptom may occur in a case where medical treatment is neglected." to [assumed symptom information] of the fixed form message 56. Accordingly, the screen generation unit 51 creates the message 60 having a content of "How is your Rocky? Tomorrow is November 18 which is reservation date for medical care. With chronic enteropathy, diarrhea, vomiting, loss of appetite, swelling of whole body, or the like may occur and a serious symptom may occur in a case where medical treatment is neglected. Please be careful tomorrow."

FIG. 9 shows the case where the current date is Nov. 23, 2019, which is five days after the scheduled hospital visit date 22. In this case, according to the message table 43, the fixed form message 56 has the content of "How is your [pet name]? There seems no hospital visit on [scheduled hospital visit date] which is previous reservation date for medical care. Drug may run out for a long time. [Chronic disease] is [assumed symptom information]. Please visit hospital immediately." Therefore, as in the cases of FIGS. 7 and 8, the screen generation unit 51 addresses "Rocky" to [pet name], "November 18" to [scheduled hospital visit date], and "chronic enteropathy" to [chronic disease] of the fixed form message 56, respectively. As in the case of FIG. 8, the screen generation unit 51 addresses "diarrhea, vomiting, loss of appetite, swelling of whole body, or the like may occur and a serious symptom may occur in a case where medical treatment is neglected." to [assumed symptom information] of the fixed form message 56. Accordingly, the screen generation unit 51 creates the message 60 having a content of "How is your Rocky? There seems no hospital visit on November 18 which is previous reservation date for medical care. Drug may run out for a long time. With chronic enteropathy, diarrhea, vomiting, loss of appetite, swelling of whole body, or the like may occur and a serious symptom may occur in a case where medical treatment is neglected. Please visit hospital immediately."

Figure 10:
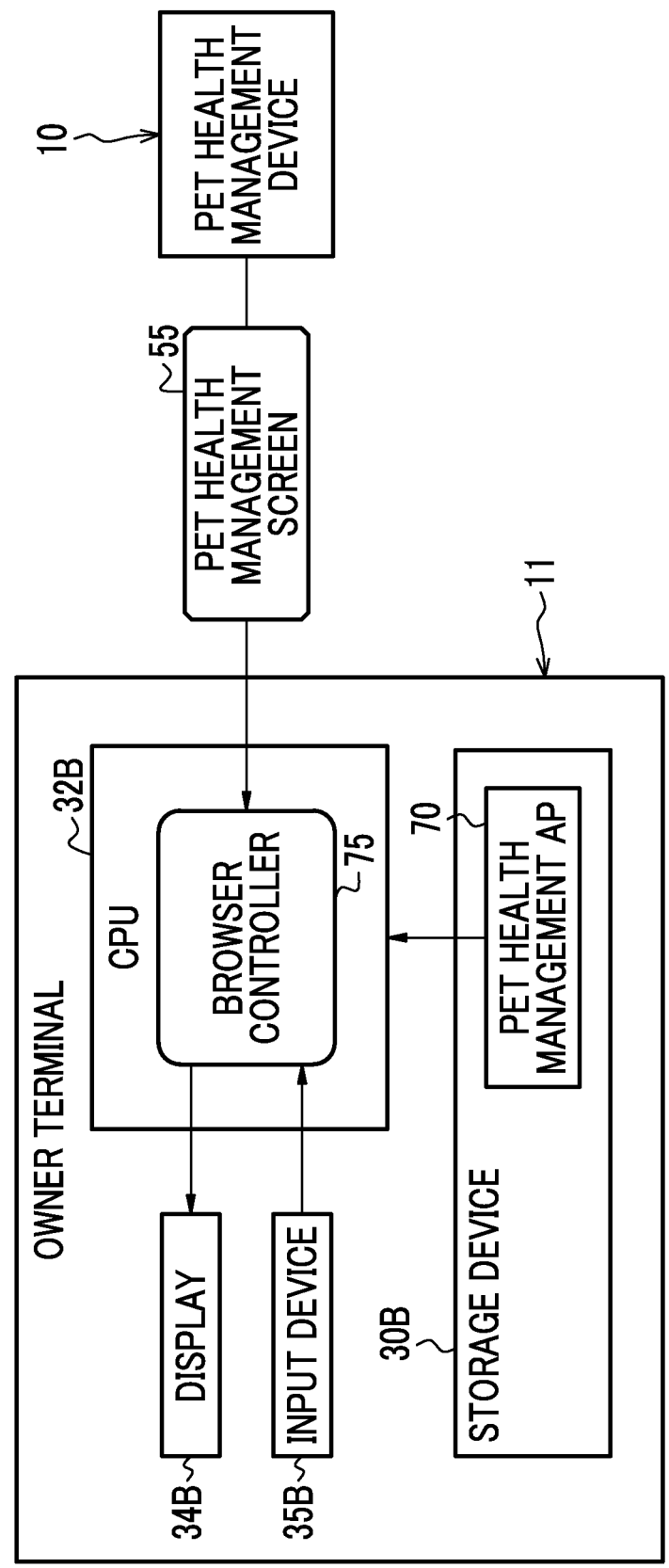
FIG. 10 is a block diagram showing a processing unit of a CPU of the owner terminal.

In FIG. 10, a pet health management AP 70 is stored in a storage device 30B of the owner terminal 11. In a case where the pet health management AP 70 is executed and the web browser is activated, a CPU 32B of the owner terminal 11 cooperates with the memory 31 and the like to function as a browser controller 75. The browser controller 75 controls the operation of the web browser. The browser controller 75 receives screen data of the various screens from the pet health management device 10. The browser controller 75 reproduces the various screens displayed on the web browser based on the screen data and displays the screens on a display 34B.

The browser controller 75 receives various operation instructions input from an input device 35B by the owner OW through the various screens. An example of the operation instruction includes an authentication instruction for access permission to the pet health management device 10. The browser controller 75 issues a request to the pet health management device 10 in response to the operation instruction. For example, the browser controller 75 issues an authentication request to the pet health management device 10 in response to the authentication instruction for the access permission to the pet health management device 10.

Figure 12:
FIG. 12 is a diagram showing a pet health management screen in the case of the example of FIG. 8.
Figure 13:
FIG. 13 is a diagram showing a pet health management screen in the case of the example of FIG. 9.

As shown in FIGS. 11 to 13, the pet health management screen 55 has a pet information display section 80, a calendar display section 81, and a message display section 82. In the pet information display section 80, the name, age, sex, and breed of the pet PT are displayed together with a face photograph thereof. In the calendar display section 81, a monthly calendar is displayed. The current date on the calendar is displayed distinctively from other dates by coloring the date as shown by hatching or the like. On a date corresponding to the scheduled hospital visit date 22, a hospital mark 83 indicating the date is displayed. On an instruction date from the doctor DR to take the prescription drug, a drug mark 84 indicating the date is displayed.

FIG. 11 shows the case where the current date is five days before the scheduled hospital visit date 22, illustrated in FIG. 7. In this case, the message 60 having the content of "How is your Rocky? There are five days left until November 18 which is next reservation date for medical care. Please do not hesitate to contact us in a case where there are any concerns about symptom." is displayed in the message display section 82.

FIG. 12 shows the case where the current date is one day before the scheduled hospital visit date 22, illustrated in FIG. 8. In this case, the message 60 having the content of "How is your Rocky? Tomorrow is November 18 which is reservation date for medical care. With chronic enteropathy, diarrhea, vomiting, loss of appetite, swelling of whole body, or the like may occur and a serious symptom may occur in a case where medical treatment is neglected. Please be careful tomorrow." is displayed in the message display section 82.

FIG. 13 shows the case where the current date is five days after the scheduled hospital visit date 22, illustrated in FIG. 9. In this case, the message 60 having the content of "How is your Rocky? There seems no hospital visit on November 18 which is previous reservation date for medical care. Drug may run out for a long time. With chronic enteropathy, diarrhea, vomiting, loss of appetite, swelling of whole body, or the like may occur and a serious symptom may occur in a case where medical treatment is neglected. Please visit hospital immediately." is displayed in the message display section 82. As described above, the screen distribution controller 52 distributes the pet health management screen 55 with the message 60 not only before the scheduled hospital visit date 22 but also after the scheduled hospital visit date 22 in the case where there is no hospital visit of the pet PT on the scheduled hospital visit date 22.

Next, an action of the above configuration will be described with reference to flowcharts of FIGS. 14 and 15. First, in the case where the operation program 40 is activated, the CPU 32A of the pet health management device 10 functions as the RW controller 50, the screen generation unit 51, and the screen distribution controller 52, as shown in FIG. 4.

Figure 14:
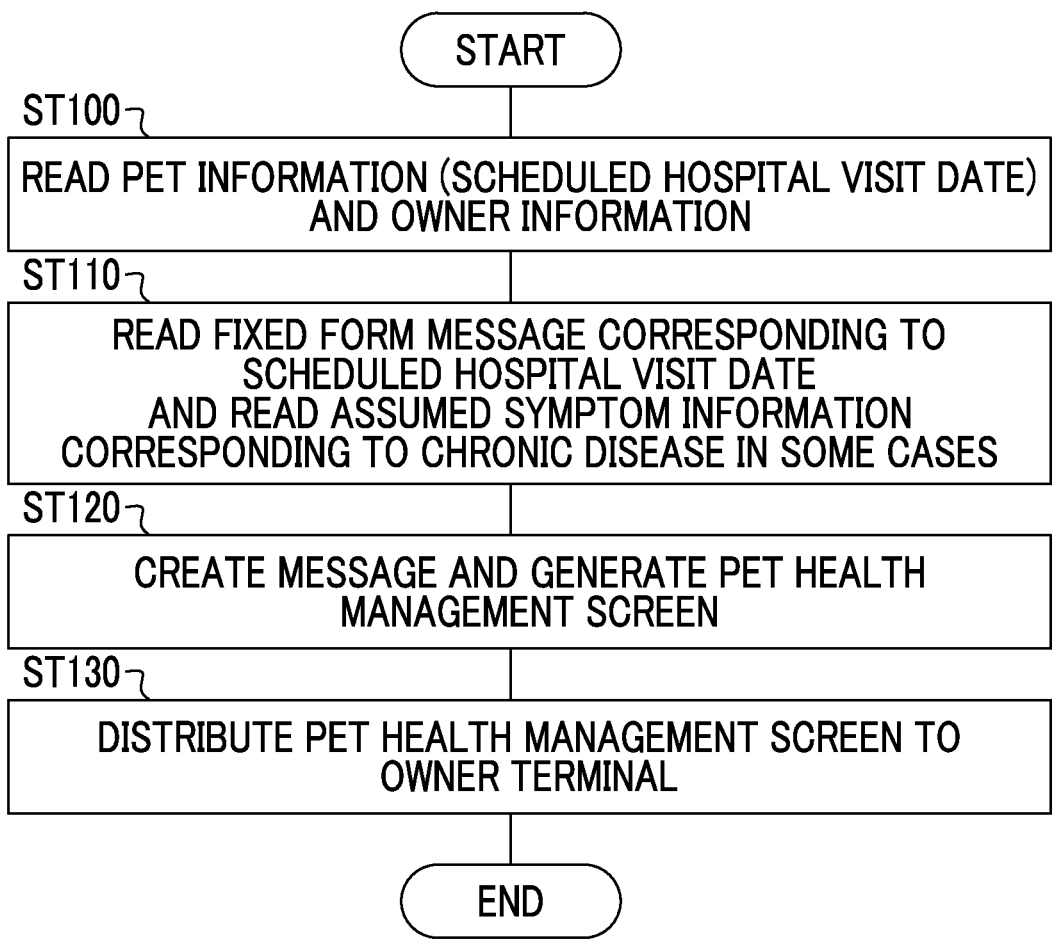
FIG. 14 is a flowchart showing a processing procedure of the pet health management device.

As shown in step ST100 in FIG. 14, the RW controller 50 reads the pet information 20 of the pet PT to which the message 60 is required to be distributed, from the storage device 30A. The RW controller 50 reads the owner information 25 associated with the pet information 20 of the pet PT to which the message 60 is required to be distributed, from the storage device 30A. The pet information 20 is output from the RW controller 50 to the screen generation unit 51. The owner information 25 is output from the RW controller 50 to the screen distribution controller 52. Step ST100 is an example of an "acquisition step" according to the technique of the present disclosure.

Next, the scheduled hospital visit date 22 registered in the pet information 20 is output from the screen generation unit 51 to the RW controller 50 as the search key. The RW controller 50 reads, from the message table 43, the fixed form message 56 corresponding to the scheduled hospital visit date 22 from the screen generation unit 51 (step ST110). The fixed form message 56 is output from the RW controller 50 to the screen generation unit 51. In a case where the current date corresponds to one day before, one day after, or five days after the scheduled hospital visit date 22, the chronic disease 21 registered in the pet information 20 is output from the screen generation unit 51 to the RW controller 50 as the search key. The RW controller 50 reads, from the assumed symptom information table 44, the assumed symptom information 57 corresponding to the chronic disease 21 from the screen generation unit 51 (step ST110). The assumed symptom information 57 is output from the RW controller 50 to the screen generation unit 51.

As shown in FIGS. 7 to 9, the screen generation unit 51 creates the message 60 based on the pet information 20, the fixed form message 56, and the assumed symptom information 57. The screen generation unit 51 generates the pet health management screen 55 in which the message 60 is displayed in the message display section 82 (step ST120). The pet health management screen 55 is output from the screen generation unit 51 to the screen distribution controller 52.

The screen distribution controller 52 distributes the pet health management screen 55 to the owner terminal 11 represented by the owner terminal identification information 26 (step ST130). Step ST130 is an example of a "distribution step" according to the technique of the present disclosure.

In the case where the pet health management AP 70 is activated in the owner terminal 11, the CPU 32B of the owner terminal 11 functions as the browser controller 75, as shown in FIG. 10.

Figure 15:
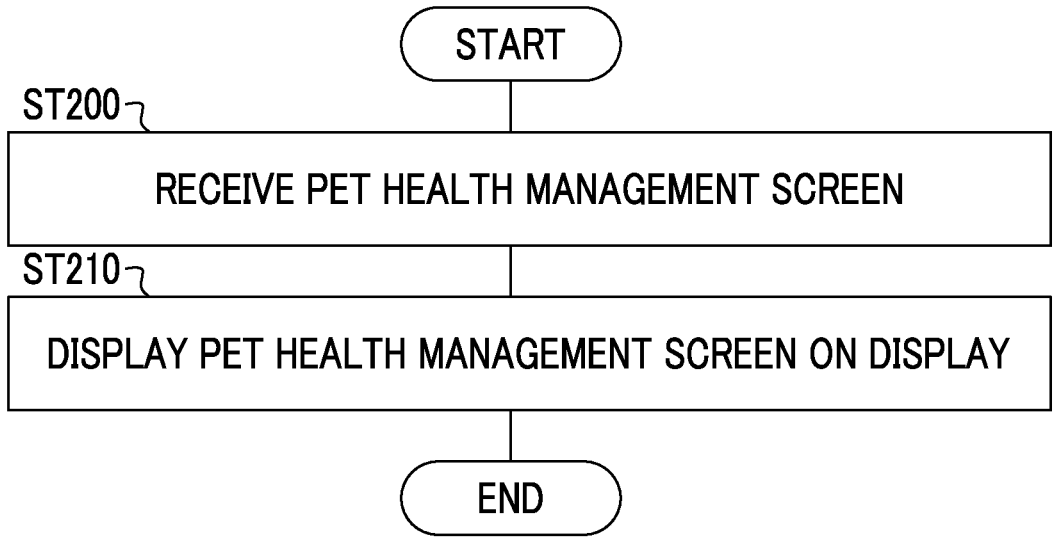
FIG. 15 is a flowchart showing a processing procedure of the owner terminal.

As shown in FIG. 15, in the owner terminal 11, the browser controller 75 receives the pet health management screen 55 from the pet health management device 10 (step ST200). The browser controller 75 displays the pet health management screen 55 on the display 34B (step ST210). Accordingly, the pet health management screen 55 is provided for the owner OW to browse. Step ST210 is an example of a "display step" according to the technique of the present disclosure.

As described above, the pet health management device 10 comprises the RW controller 50 as an acquisition unit and the screen distribution controller 52 as a distribution controller. The RW controller 50 reads the pet information 20 from the storage device 30A to acquire the scheduled hospital visit date 22 of the pet PT to the animal hospital 13. The screen distribution controller 52 distributes the pet health management screen 55 with the message 60 prompting the hospital visit of the pet PT and including the assumed symptom information 57 to the owner terminal 11 according to the scheduled hospital visit date 22. Therefore, it is possible to appropriately predict the symptom of the pet PT that is difficult to grasp and thus to increase the feeling of the owner OW to bring the pet PT to the animal hospital 13, as compared with the case where the assumed symptom information 57 is not present. That is, it is possible to more strongly motivate the owner OW to bring the pet PT to the animal hospital 13.

The screen distribution controller 52 distributes the pet health management screen 55 with the message 60 not only before the scheduled hospital visit date 22 but also after the scheduled hospital visit date 22 in the case where there is no hospital visit of the pet PT on the scheduled hospital visit date 22. Therefore, it is possible to surely notify the owner OW who forgets the scheduled hospital visit date 22 or the owner OW who ignores the scheduled hospital visit date 22 that the pet PT needs to be brought to the animal hospital 13.

Further, the assumed symptom information 57 may or may not be included in the message 60 depending on the difference between the scheduled hospital visit date 22 and the distribution date. Therefore, as in this example, it is possible to differentiate the content of the message 60 depending on situations such as not including the assumed symptom information 57 in the message 60 in a situation where the current date is not so imminent, which is five days before the scheduled hospital visit date 22, and including the assumed symptom information 57 in the message 60 in other cases. The assumed symptom information 57 may be not included in the message 60 in a case where the current date is before the scheduled hospital visit date 22, and the assumed symptom information 57 may be included in the message 60 in a case where the current date is after the scheduled hospital visit date 22. Alternatively, the assumed symptom information 57 may be included in the message 60 in all situations regardless of the difference between the scheduled hospital visit date 22 and the distribution date.

The pet health management screen 55 is displayed on the display 34B of the owner terminal 11. Therefore, it is possible for the owner OW to easily recognize the message 60 and thus the assumed symptom information 57.

Second Embodiment

In the above first embodiment, an example is shown in which the distribution frequency of the pet health management screen 55 with the message 60 is the same before the scheduled hospital visit date 22 and after the scheduled hospital visit date 22, but the present invention is not limited thereto. As in a second embodiment shown in FIGS. 16A and 16B, the distribution frequency of the pet health management screen 55 with the message 60 may be different before the scheduled hospital visit date 22 and after the scheduled hospital visit date 22.

Figure 16A:
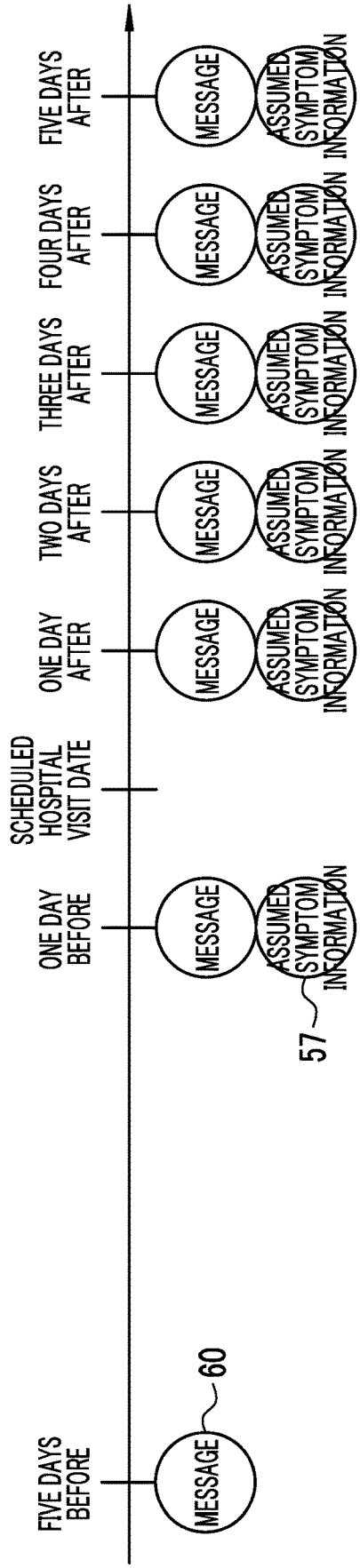
FIGS. 16A and 16B are diagrams showing a second embodiment in which a distribution frequency of message information is different before the scheduled hospital visit date and after the scheduled hospital visit date.

FIG. 16A is an example in which the screen distribution controller 52 increases the distribution frequency of the pet health management screen 55 with the message 60 to be distributed after the scheduled hospital visit date 22 as compared with the distribution frequency of the pet health management screen 55 with the message 60 to be distributed before the scheduled hospital visit date 22. Specifically, before the scheduled hospital visit date 22, the screen distribution controller 52 distributes the pet health management screen 55 with the message 60 twice five days before and one day before the scheduled hospital visit date 22. On the contrary, after the scheduled hospital visit date 22, the screen distribution controller 52 distributes the pet health management screen 55 with the message 60 five times one day after to five days after the scheduled hospital visit date 22. The assumed symptom information 57 is included in the message 60 except in the case of five days before the scheduled hospital visit date 22. With the distribution method of the pet health management screen 55 with the message 60 described above, it is possible to increase the opportunity to motivate the owner OW who forgets the scheduled hospital visit date 22 or the owner OW who ignores the scheduled hospital visit date 22 to bring the pet PT to the animal hospital 13.

Figure 16B:
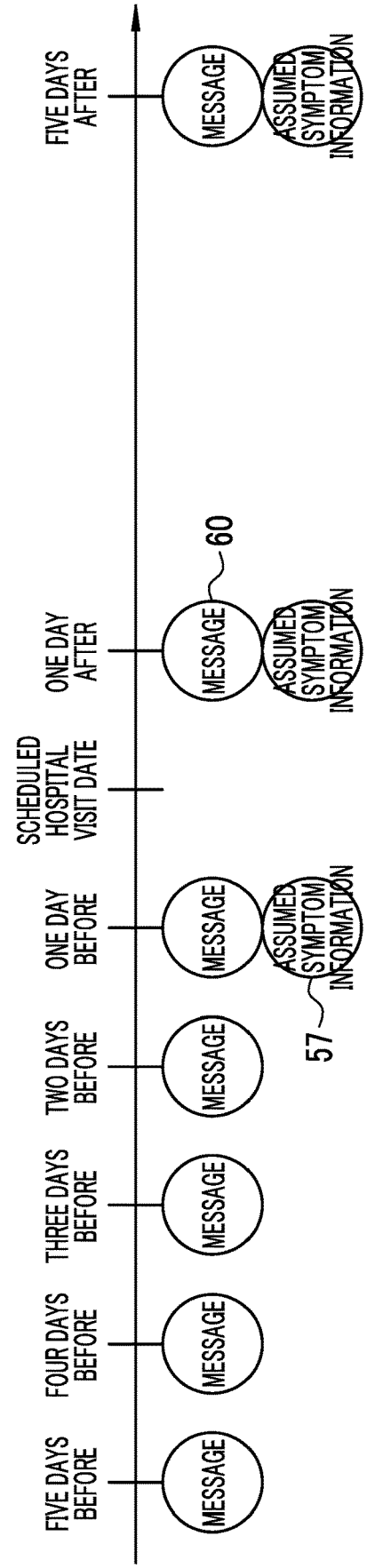

In contrast to the case of FIG. 16A, FIG. 16B is an example in which the screen distribution controller 52 decreases the distribution frequency of the pet health management screen 55 with the message 60 to be distributed after the scheduled hospital visit date 22 as compared with the distribution frequency of the pet health management screen 55 with the message 60 to be distributed before the scheduled hospital visit date 22. Specifically, before the scheduled hospital visit date 22, the screen distribution controller 52 distributes the pet health management screen 55 with the message 60 five times five days before to one day before the scheduled hospital visit date 22. On the contrary, after the scheduled hospital visit date 22, the screen distribution controller 52 distributes the pet health management screen 55 with the message 60 twice one day after and five days after the scheduled hospital visit date 22. The assumed symptom information 57 is included in the message 60 in the case of one day before, one day after, and five days after the scheduled hospital visit date 22. With the distribution method of the pet health management screen 55 with the message 60 described above, the owner OW can be made more strongly aware of the scheduled hospital visit date 22 and thus the risk of the owner OW forgetting the scheduled hospital visit date 22 can be reduced.

Third Embodiment

Figure 17:
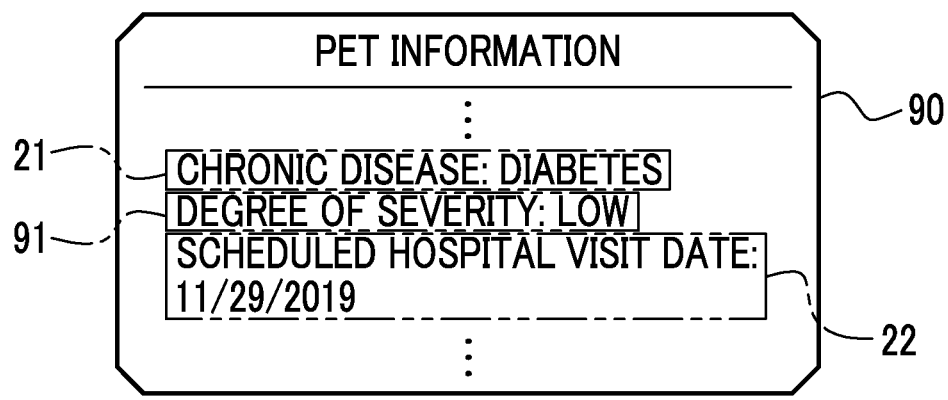
FIG. 17 is a diagram showing pet information according to a third embodiment.

In a third embodiment shown in FIG. 17 and FIGS. 18A and 18B, the distribution frequency of the pet health management screen 55 with the message 60 increase as a degree of severity of the chronic disease 21 is higher.

As shown in FIG. 17, a degree of severity 91 of the chronic disease 21 is registered in pet information 90 of the third embodiment, in addition to the chronic disease 21, the scheduled hospital visit date 22, and the like. The degree of severity 91 has, for example, three levels of low, medium, and high, and is input by the doctor DR. FIG. 17 illustrates a case where the chronic disease 21 is "diabetes" and the degree of severity 91 is "low".

Figure 18C:
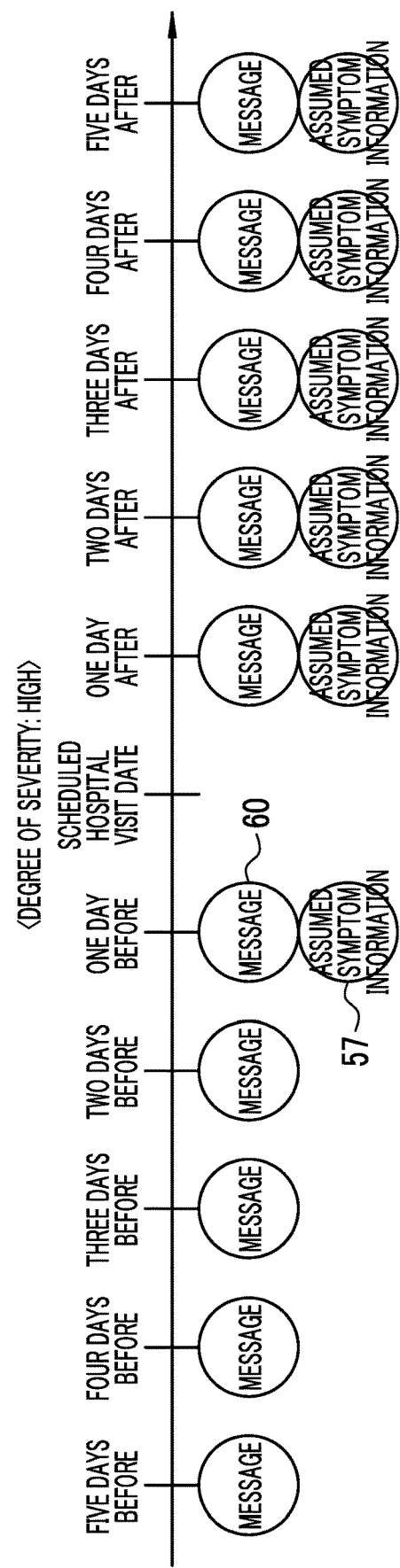
FIG. 18C shows a case where the degree of severity is "high", respectively.

FIGS. 18A and 18B show the distribution frequency of the pet health management screen 55 with the message 60 according to the degree of severity 91. FIG. 18A shows the case where the degree of severity 91 is "low", FIG. 18B shows a case where the degree of severity 91 is "medium", and FIG. 18C shows a case where the degree of severity 91 is "high".

In the case of FIG. 18A, the screen distribution controller 52 distributes the pet health management screen 55 with the message 60 twice in total one day before and one day after the scheduled hospital visit date 22. The assumed symptom information 57 is included in the message 60 in all cases of one day before and one day after the scheduled hospital visit date 22.

In the case of FIG. 18B, the screen distribution controller 52 distributes the pet health management screen 55 with the message 60 six times in total five days before, three days before, three days after, and five days after the scheduled hospital visit date 22, in addition to one day before and one day after the scheduled hospital visit date 22 in the case of FIG. 18A. The assumed symptom information 57 is included in the message 60 except in the cases of five days before and three days before the scheduled hospital visit date 22.

In the case of FIG. 18C, the screen distribution controller 52 distributes the pet health management screen 55 with the message 60 ten times in total four days before, two days before, two days after, and four days after the scheduled hospital visit date 22, in addition to five days before, three days before, one day before, one day after, three days after, and five days after the scheduled hospital visit date 22 in the case of FIG. 18B. The assumed symptom information 57 is included in the message 60 except in the cases of five days before to two days before the scheduled hospital visit date 22.

As described above, in the third embodiment, the screen distribution controller 52 increases the distribution frequency of the pet health management screen 55 with the message 60 as the degree of severity 91 of the chronic disease 21 is higher. Therefore, it is possible to furthermore strongly motivate the owner OW of the pet PT with a higher degree of severity 91 of the chronic disease 21 and more need for the hospital visit to bring the pet PT to the hospital.

Fourth Embodiment

In a fourth embodiment shown in FIG. 19, the assumed symptom information 57 for the same chronic disease 21 differs depending on the breed of the pet PT.

As shown in FIG. 19, an assumed symptom information table 100 of the fourth embodiment includes an item for the breed of pet PT. The assumed symptom information 57 for the same chronic disease 21 differs depending on the breed of the pet PT. For example, in a case where the chronic disease 21 is chronic enteropathy, the assumed symptom information 57 differs depending on whether the breed is Shiba Inu or other cases. More specifically, in a case where the breed is Shiba Inu, "Shiba Inu requires particularly careful follow-up observation" is added to "diarrhea, vomiting, loss of appetite, swelling of whole body, or the like may occur and a serious symptom may occur in a case where medical treatment is neglected." This is because the reason for this "Shiba Inu requires particularly careful follow-up observation" is that it is clear from medical knowledge such as a past medical paper that a prognosis of chronic enteropathy is particularly poor in Shiba Inu.

In a case where the chronic disease 21 is diabetes, the assumed symptom information 57 differs depending on whether the breed is Beagle, Poodle, Dachshund, and Miniature Schnauzer or not. More specifically, in the case where the breed is Beagle, Poodle, Dachshund, and Miniature Schnauzer, "Beagle, Poodle, Dachshund, and Miniature Schnauzer are prone to congenital causes and need special attention" is added to "frequent urination, diarrhea, vomiting, weight loss, or the like may occur and complications such as cataract, gangrene, neuropathy, and liver dysfunction develop in a case where medical treatment is neglected." This is because the reason for this "Beagle, Poodle, Dachshund, and Miniature Schnauzer are prone to congenital causes and need special attention" is also clear from medical knowledge.

As described above, in the fourth embodiment, the assumed symptom information 57 for the same chronic disease 21 differs depending on the breed of the pet PT. Therefore, it is possible to distribute the message 60 including the assumed symptom information 57 suitable for the breed.

Figure 20:
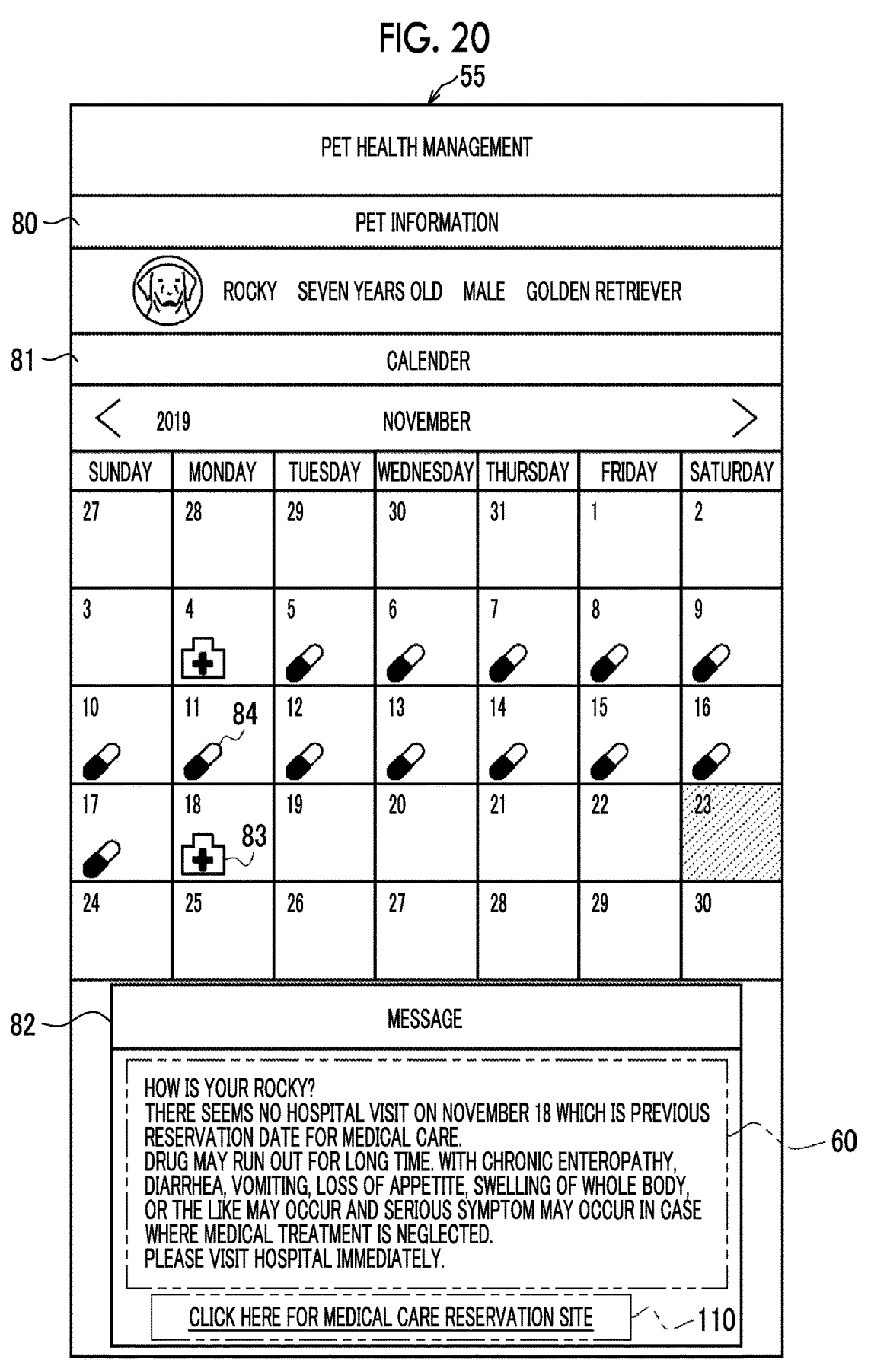

As shown in FIG. 20, on the pet health management screen 55 to be distributed after no hospital visit of the pet PT on the scheduled hospital visit date 22, a link 110 to the medical care reservation site of the animal hospital 13 may be displayed below the message 60 in the message display section 82. With the display, the owner OW who forgets the scheduled hospital visit date 22 or the owner OW who ignores the scheduled hospital visit date 22 can easily make the medical care reservation again.

On the pet health management screen 55, the assumed symptom information 57 may be displayed in bold or red to distinguish the information from another piece of information.

In each of the above embodiments, the form of distributing the pet health management screen 55 is employed as a form of distributing the message information, but the present invention is not limited thereto. A form in which the message 60 itself is distributed as message information by electronic mail may be employed. In this case, an email address is registered in the owner terminal identification information 26. A timing of distributing the message 60 may be configured to be settable by the animal hospital 13 side.

The message information distributed from the pet health management device 10 to the owner terminal 11 is not limited to the pet health management screen 55 with the message 60 or the message 60 itself. For example, the message table 43 and the assumed symptom information table 44 are stored in the storage device 30B of the owner terminal 11. The browser controller 75 of the owner terminal 11 carries out the function of the screen generation unit 51. The pet health management device 10 distributes the pet information 20 and a code indicating the chronic disease 21 and the scheduled hospital visit date 22 as message information to the owner terminal 11. The browser controller 75 of the owner terminal 11 reads the message 60 corresponding to the code indicating the scheduled hospital visit date 22 from the message table 43 to the browser controller 75. In some cases, the assumed symptom information 57 corresponding to the code indicating the chronic disease 21 is read from the assumed symptom information table 44. The browser controller 75 generates the pet health management screen 55 with the message 60 and displays the screen on the display 34B. As described above, the message information may be a data code for generating the message 60 in the owner terminal 11, and various forms can be considered.

On the pet health management screen 55, the owner OW may input whether or not the pet PT takes the prescription drug. In a case where the prescription drug is not taken as prescribed usage, a warning prompting the drug-taking may be displayed. A remaining amount of the prescription drug may be managed, and a date on which the prescription drug is expected to run out may be set as the scheduled hospital visit date.

In each of the above embodiments, the smartphone is illustrated as the owner terminal 11, but the owner terminal 11 is not limited thereto. A tablet terminal may be used as the owner terminal 11.

The animal species of the pet PT is not limited to the dog and cat exemplified in each of the above embodiments. The animal species of the pet PT may be a bird, rabbit, hamster, or the like.

A hardware configuration of the computer configuring the pet health management device 10 may be modified in various ways. For example, the pet health management device 10 may be configured of a plurality of computers separated as hardware for the purpose of improving processing capacity and reliability. Specifically, the functions of the screen generation unit 51 and the screen distribution controller 52 are carried out by distributed two server computers. In this case, the pet health management device 10 is configured of the two server computers.

As described above, the hardware configuration of the computer may be changed as appropriate according to the required performance such as processing capacity, safety, and reliability. Not only the hardware but also the AP such as the operation program 40 may be duplicated or stored in a plurality of storage devices in a distributed manner for the purpose of ensuring safety and reliability.

In each of the above embodiments, the pet health management device 10 is used in the plurality of animal hospitals 13. However, the pet health management device 10 may be used in one animal hospital 13. In this case, the hospital terminal 14 may carry out the function of the pet health management device 10.

In each of the above embodiments, for example, a hardware structure of a processing unit that executes various types of processing such as the RW controller 50, the screen generation unit 51, the screen distribution controller 52, and the browser controller 75 can use the following various processors. The various processors include a programmable logic device (PLD) which is a processor whose circuit configuration is changeable after manufacturing such as a field-programmable gate array (FPGA) and/or a dedicated electric circuit which is a processor having a circuit configuration exclusively designed to execute specific processing such as an application specific integrated circuit (ASIC), and the like, in addition to the CPUs 32A and 32B which are general-purpose processors that execute software (operation program 40 and pet health management AP 70) to function as various processing units.

One processing unit may be configured by one of the various types of processors or may be configured by a combination of two or more processors of the same type or different types (for example, a combination of a plurality of FPGAs and/or a combination of a CPU and an FPGA). A plurality of processing units may be configured by one processor.

As an example of configuring the plurality of processing units with one processor, first, there is a form in which one processor is configured by a combination of one or more CPUs and software and the processor functions as the plurality of processing units, as represented by computers such as a client and a server. Second, there is a form in which a processor that realizes the functions of the entire system including the plurality of processing units with one integrated circuit (IC) chip is used, as represented by a system-on-chip (SoC) or the like. As described above, the various processing units are configured using one or more of the various processors as the hardware structure.

More specifically, a circuitry combining circuit elements such as semiconductor elements may be used as the hardware structure of the various processors.

From the above description, it is possible to grasp the invention described in appendix 1 below.

Appendix 1

A hospital visit support device comprising:
an acquisition processor that acquires a scheduled hospital visit date to an animal hospital of a pet suffering from a chronic disease; and
a distribution control processor that controls a distribution of message information related to a message prompting a hospital visit of the pet and including assumed symptom information indicating a symptom assumed in a case where there is no hospital visit of the pet on the scheduled hospital visit date, to an owner terminal owned by an owner of the pet according to the scheduled hospital visit date.

The above various embodiments and/or various modifications can be combined as appropriate in the technique of the present disclosure. It is needless to say that the technique of the present disclosure is not limited to each of the above embodiments and various configurations can be employed without departing from the gist. The technique of the present disclosure extends to a storage medium that stores the program non-transitorily, in addition to the program.

The description content and the illustrated content described above are detailed descriptions of portions related to the technique of the present disclosure and are merely an example of the technique of the present disclosure. For example, the above description of the configurations, functions, actions, and effects is an example of the configurations, functions, actions, and effects of the portions according to the technique of the present disclosure. Therefore, it is needless to say that an unnecessary part may be deleted, a new element may be added, or a replacement may be performed to the description content and the illustrated content described above within a scope not departing from the gist of the technique of the present disclosure. In order to avoid complication and facilitate understanding of the portion related to the technique of the present disclosure, the description related to common general knowledge not requiring special description in order to implement the technique of the present disclosure is omitted in the above description content and illustrated content.

In the present specification, "A and/or B" is synonymous with "at least one of A or B". That is, "A and/or B" means that only A may be used, only B may be used, or a combination of A and B may be used. In the present specification, the same concept as "A and/or B" is also applied to a case where three or more matters are linked and expressed by "and/or".

All documents, patent applications, and technical standards described in this specification are incorporated by reference in this specification to the same extent as in a case where the incorporation of each individual document, patent application, and technical standard by reference is specifically and individually described.

Explanation of References

What is claimed is:

1. A hospital visit support device comprising:
    an acquisition unit that acquires a scheduled hospital visit date to an animal hospital of a pet suffering from a chronic disease; and
    a distribution controller that controls a distribution of message information related to a message prompting a hospital visit of the pet and including assumed symptom information indicating a symptom assumed in a case where there is no hospital visit of the pet on the scheduled hospital visit date, to an owner terminal owned by an owner of the pet according to the scheduled hospital visit date,
    wherein the distribution controller increases a distribution frequency of the message information as a degree of severity of the chronic disease is higher.

2. The hospital visit support device according to claim 1, wherein the distribution controller distributes the message information also after the scheduled hospital visit date in the case where there is no hospital visit of the pet on the scheduled hospital visit date, in addition to before the scheduled hospital visit date.

3. The hospital visit support device according to claim 2, wherein the distribution controller differentiates a distribution frequency of the message information distributed before the scheduled hospital visit date and a distribution frequency of the message information distributed after the scheduled hospital visit date.

4. The hospital visit support device according to claim 1, wherein there are cases where the message includes and does not include the assumed symptom information depending on a difference between the scheduled hospital visit date and a distribution date of the message information.

5. The hospital visit support device according to claim 1, wherein the assumed symptom information for the same chronic disease differs depending on a breed of the pet.

6. A hospital visit support method comprising:
    an acquisition step of acquiring a scheduled hospital visit date to an animal hospital of a pet suffering from a chronic disease; and
    a distribution step of distributing message information related to a message prompting a hospital visit of the pet and including assumed symptom information indicating a symptom assumed in a case where there is no hospital visit of the pet on the scheduled hospital visit date, to an owner of the pet according to the scheduled hospital visit date,
    wherein the distribution step includes increasing a distribution frequency of the message information as a degree of severity of the chronic disease increases.

7. The hospital visit support method according to claim 6, further comprising:
    a display step of performing a display based on the distributed message information.

8. A non-transitory computer-readable storage medium storing a hospital visit support program causing a computer to function as:
    an acquisition unit that acquires a scheduled hospital visit date to an animal hospital of a pet suffering from a chronic disease; and
    a distribution controller that controls a distribution of message information related to a message prompting a hospital visit of the pet and including assumed symptom information indicating a symptom assumed in a case where there is no hospital visit of the pet on the scheduled hospital visit date, to an owner terminal owned by an owner of the pet according to the scheduled hospital visit date,
    wherein the distribution controller increases a distribution frequency of the message information as a degree of severity of the chronic disease is higher.

9. A hospital visit support system comprising:
    a hospital visit support device that:
        acquires a scheduled hospital visit date to an animal hospital of a pet suffering from a chronic disease, and
        distributes message information related to a message prompting a hospital visit of the pet and including assumed symptom information indicating a symptom assumed in a case where there is no hospital visit of the pet on the scheduled hospital visit date, according to the scheduled hospital visit date,
        wherein a distribution frequency of the message information is increased as a degree of severity of the chronic disease increases; and
    an owner terminal that is owned by an owner of the pet and performs a display based on the distributed message information.

* * * * *